United States Patent [19]
Reisdorf et al.

[11] Patent Number: 5,989,183
[45] Date of Patent: Nov. 23, 1999

[54] DISPOSABLE ENDOSCOPE SHEATH

[75] Inventors: Dennis Reisdorf; William Donofrio, both of Jacksonville, Fla.

[73] Assignee: Xomed Surgical Products, Inc., Jacksonville, Fla.

[21] Appl. No.: 09/129,180

[22] Filed: Jun. 5, 1998

Related U.S. Application Data

[63] Continuation of application No. 08/095,975, Jul. 22, 1993, abandoned.

[51] Int. Cl.$^6$ ........................................... A61B 1/12
[52] U.S. Cl. ..................... 600/156; 600/121; 600/153; 600/157
[58] Field of Search ................................ 600/121, 123, 600/153, 155, 156, 157

[56] References Cited

U.S. PATENT DOCUMENTS

| | | |
|---|---|---|
| 4,132,227 | 1/1979 | Ibe . |
| 4,281,646 | 8/1981 | Kinoshita . |
| 4,721,097 | 1/1988 | D'Amelio . |
| 4,741,326 | 5/1988 | Sidall et al. . |
| 4,860,731 | 8/1989 | Matsuura . |
| 4,869,238 | 9/1989 | Opie et al. . |
| 4,878,485 | 11/1989 | Adair . |
| 4,881,523 | 11/1989 | Heckele . |
| 4,973,311 | 11/1990 | Iwakoshi et al. . |
| 4,974,580 | 12/1990 | Anapliotis . |
| 4,991,564 | 2/1991 | Takahashi et al. . |
| 4,991,565 | 2/1991 | Takahashi et al. . |
| 5,050,585 | 9/1991 | Takahashi . |
| 5,154,164 | 10/1992 | Chikama . |
| 5,154,166 | 10/1992 | Chikama . |
| 5,159,919 | 11/1992 | Chikama . |
| 5,225,001 | 7/1993 | Manni et al. . |
| 5,237,984 | 8/1993 | Williams, III et al. . |
| 5,287,845 | 2/1994 | Faul et al. . |
| 5,313,934 | 5/1994 | Wiita et al. . |
| 5,320,091 | 6/1994 | Grossi et al. . |
| 5,400,767 | 3/1995 | Murdoch . |

*Primary Examiner*—John P. Leubecker

[57] ABSTRACT

The disposable endoscope sheath includes a low-profile sleeve member that cooperates with the endoscope shaft to establish a relatively narrow irrigation space between the sleeve member and the endoscope shaft. The sleeve member is intentionally shorter than the endoscope shaft to accommodate a variety of different endoscope lengths that are longer than the sleeve. In various embodiments of the invention the sleeve member can be positioned to establish a predetermined distal gap between the terminal end of the sleeve member and the viewing end of the endoscope shaft, to establish a flush alignment between the respective ends, or to have the endoscope shaft project slightly beyond the terminal end of the sleeve member. Irrigation fluid can thus flow across the viewing end of the endoscope flushing away surgical debris from the viewing end. The sleeve member can be a rigid or flexible structure. The size of the irrigation space is sized to permit retention of irrigation solution in the irrigation space when irrigation fluid is no longer being directed into the irrigation space.

15 Claims, 7 Drawing Sheets

DISPOSABLE ENDOSCOPE SHEATH

This application is a continuation application of application Ser. No. 08/095,975, filed Jul. 22, 1993, now abandoned.

BACKGROUND OF THE INVENTION

This invention is directed to disposable sheaths for endoscopes and more particularly to a low profile disposable sheath that provides effective flushing of surgical debris from the viewing end of an endoscope.

The term surgical debris is intended to refer to any body material such as blood or tissue that lands on the viewing end of an endoscope during surgery and obscures the field of view through the endoscope.

Endoscopes permit remote visual examination of a surgical site while a surgical procedure is being performed. During surgery, blood, tissue or other bodily material from the surgical site can splatter onto the viewing end of the endoscope and obscure the field of view through the endoscope.

In some instances it is necessary to remove the endoscope from the surgical site to clean the viewing end, which usually interrupts and undesirably prolongs a surgical procedure.

Because of the inconvenience of removing and cleaning an endoscope during surgery, some surgeons prefer to use an endoscope with a sheath that has provision for flushing away any surgical debris that obscures the view through the endoscope.

Known endoscope sheaths, such as shown in U.S. Pat. Nos. 4,991,565 and 4,974,580, are usually custom fitted to the endoscope. The sheath can include air tubes, water tubes and suction tubes to flush away or suction out surgical debris from the viewing end of the endoscope. The irrigation, suction and air tubes on the endoscope sheath can add significant girth to the profile of the endoscope and require an incision of corresponding size to accommodate the endoscope and sheath.

Since many endoscopes are of different length, a diversity of different size sheaths are required to custom fit each different length of endoscope with a sheath. Large inventories of customized endoscope sheaths of different length are generally maintained to ensure compatibility with each different endoscope.

It is thus desirable to provide a low profile endoscope sheath that is adaptable to a variety of different endoscope lengths and can effectively flush debris from the viewing end of the endoscope.

OBJECTS AND SUMMARY OF THE INVENTION

Among the several objects of the invention may be noted the provision of a novel endoscope sheath, a novel low profile disposable endoscope sheath for flushing debris from the viewing end of an endoscope, a novel disposable endoscope sheath that can be adapted for use with endoscope barrels or shafts of different length, a novel disposable endoscope sheath that enables irrigating fluid to flow onto the viewing end of the endoscope, a novel disposable endoscope sheath that holds an endoscope barrel at a predetermined retracted position in a sheath to optimize the debris cleaning action furnished by irrigating fluid, a novel disposable endoscope sheath that establishes an optimum gap between the sheath and the viewing end of the endoscope to provide optimum flushing of debris from the viewing end of the endoscope, a novel disposable endoscope sheath that locates an endoscope barrel in a predetermined position in the sheath, a novel disposable endoscope sheath with centering structure for centering the endoscope barrel or shaft within the sheath, a novel disposable endoscope sheath with spacer structure for spacing the endoscope shaft from a terminal end of the endoscope sheath, a novel endoscope sheath for a flexible endoscope and a novel method of cleaning surgical debris from the viewing end of an endoscope.

Other objects and features of the invention will be in part apparent and in part pointed out hereinafter.

In accordance with the invention, the disposable sheath for an endoscope includes a sleeve housing that receives a body portion of the endoscope and a sleeve member, that receives the endoscope shaft.

The sleeve member which depends from the sleeve housing is generally circular in cross section and has a predetermined length that is shorter than the length of the endoscope shaft. The inner diameter of the sleeve member is sized to slidably accommodate the endoscope shaft such that an irrigation space is defined between the endoscope shaft and the sleeve member.

A distal portion of the sleeve member includes means to locate the viewing end of the endoscope shaft in a predetermined recessed position in the sleeve. A distal gap of predetermined magnitude is thus established between the terminal end of the sleeve member and the viewing end of the endoscope.

Irrigating solution that is directed into the irrigation space can flow into the distal gap and onto the viewing end of the endoscope to flush debris from the viewing end of the endoscope.

In several embodiments of the invention the terminal end of the sleeve, which has at least one opening, includes a terminal end flange that prevents passage of the endoscope shaft beyond the terminal end opening.

The sleeve member is shorter in length than the endoscope shaft to ensure that the terminal end of the endoscope shaft bottoms against the terminal flange of the sleeve member. The sleeve member is thus intended for use with a diversity of endoscope shafts that are longer than the sleeve member.

In some embodiments of the invention a spacer member such as a spacer dimple is provided on the terminal end flange of the sleeve member. The spacer member enables the terminal end of the endoscope shaft to be stepped away from the terminal end flange of the sleeve member. The terminal end flange can thus divert irrigation fluid from the irrigation channel into the distal gap to flow across the viewing end of the endoscope and flush away surgical debris from the viewing end of the endoscope.

Other embodiments of the invention include spacer members projecting from a distal wall portion of the sleeve member to engage with and prevent the terminal end of the endoscope from extending beyond a terminal end of the sleeve member. The projecting spacer members establish a desirable distal gap between the terminal end of the sleeve member and the terminal end of the endoscope shaft. Irrigation fluid can thus flow into the distal gap and onto the terminal end of the endoscope shaft to flush away debris.

Any of the embodiments of the invention can be made of flexible material to adapt to a flexible endoscope. An accordion or bellows structure can be incorporated in the sleeve member to yield to sharp curves of the endoscope shaft.

A further embodiment of the invention includes a sleeve member that has splines or spines formed therein. The spines provide a sufficient grip on the endoscope shaft to maintain the endoscope shaft at a selected predetermined location. Thus the endoscope shaft can be slidably inserted to the end of the sleeve member and then retracted slightly to provide a desirable distal gap. Irrigation fluid flows through the distal gap to provide a cleansing action of the viewing end of the endoscope shaft.

If desired, a flange structure and/or a dimple structure can be provided at a distal portion of the sleeve member in combination with the spines to prevent the terminal end of the endoscope shaft from passing through the terminal end of the sleeve member.

Any of the embodiments of the invention can include centering members such as dimples that project from an interior surface of the sleeve member to engage an exterior surface of the endoscope shaft.

In addition, any of the embodiments of the invention can be provided with a sleeve member having a terminal end that is inclined a predetermined angle with respect to a longitudinal axis of the sleeve member, such as an angle of 5–70°.

The invention accordingly comprises the constructions and method hereinafter described, the scope of the invention being indicated in the claims.

DESCRIPTION OF THE DRAWINGS

In the accompanying drawings.

Corresponding reference characters indicate corresponding parts throughout the several views of the drawings.

DETAILED DESCRIPTION OF THE INVENTION

Figure 1:
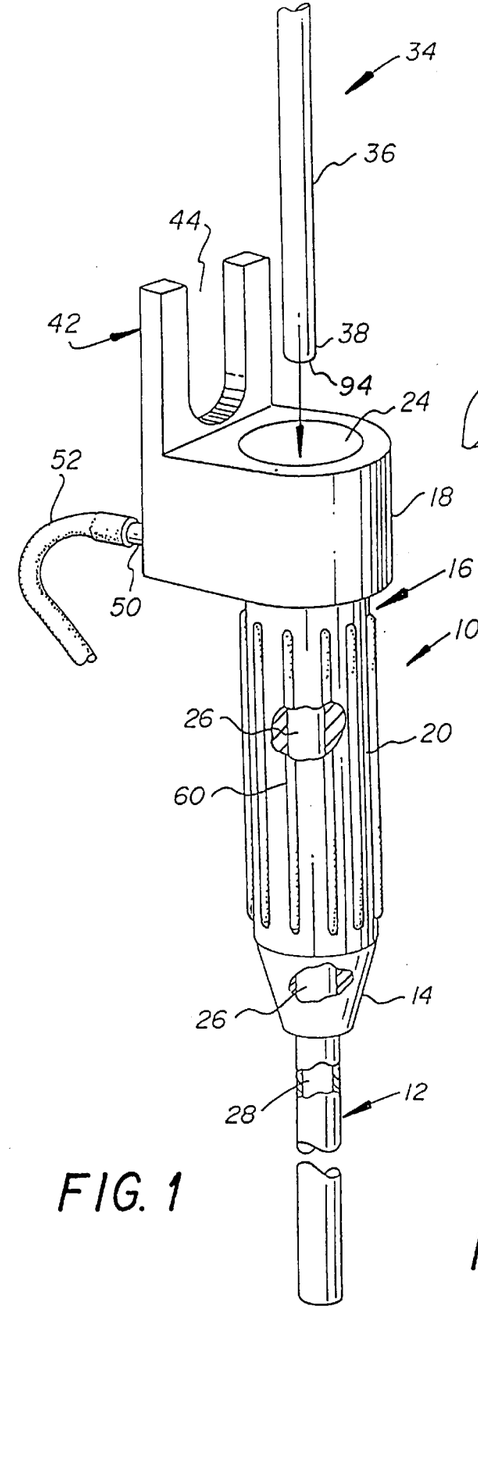
FIG. 1 is a simplified schematic perspective view of a disposable endoscope sheath including a sleeve housing and a sleeve member, prior to reception of an endoscope.

A disposable sheath incorporating one embodiment of the invention is generally indicated by the reference number 10 in FIG. 1.

The sheath 10 includes an elongated sleeve member 12 joined to an end portion 14 of a sleeve housing 16 that is preferably formed of a plastic such as acrylonitrile-butadiene-styrene. The sleeve housing 16 includes a collar portion 18 with a depending body portion 20 that facilitates handling of the sheath 10.

Figure 2:
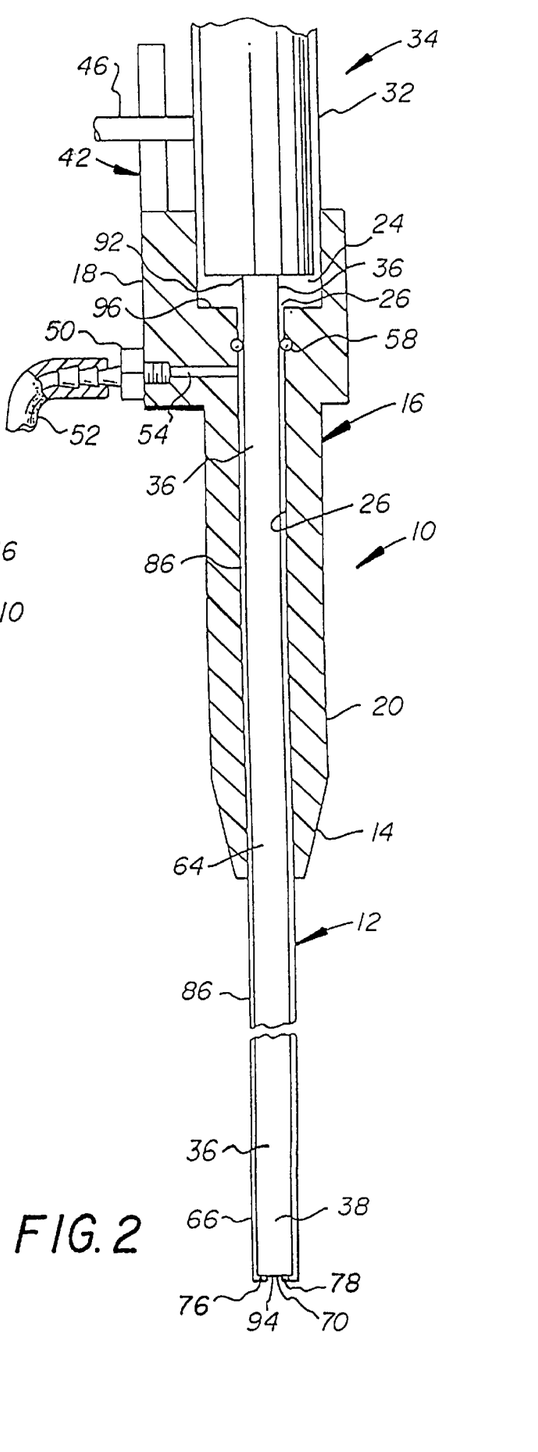
FIG. 2 is a sectional view thereof showing an endoscope being received in the sheath.

A recess 24 in the collar portion 18 communicates with a bore 26 in the body portion 20, the bore 26 communicating with the hollow interior 28 (FIG. 1) of the sleeve member 12. As shown in FIG. 2, the recess 24 is adapted to receive a housing 32 of an endoscope 34. A shaft 36 of the endoscope 34 is insertable in the bore 26 and in the hollow interior 28 of the sleeve member 12. The recess 24 can be of any shape that complements the shape of the endoscope housing 32.

Although not shown, the endoscope shaft 36 contains a light transmitting member and a lens, the lens being provided at a distal end portion 38 of the shaft 36.

The collar portion 18 further includes an upwardly extending yoke member 42 with a mouth 44 for securely holding the endoscope housing light port (not shown) to prevent rotation of the shaft 36.

An irrigation fitting 50 joined to the collar portion 18 supports an irrigation tube 52. The tube 52 communicates with the bore 26 in the body portion 20 through a fluid passage 54 in the collar portion 18. An O-ring 58 in the collar portion 18 is adapted to surround the endoscope shaft 36 to prevent fluid regression from the bore 26 into the recess 24. Grip assist elements 60 are formed on the body portion 20 to facilitate manual handling thereof.

The sleeve member 12 is a rigid structure of generally tubular shape preferably formed of thin-walled metal or plastic having a wall thickness of approximately 0.001 to 0.012 inches. A fully open proximal end 64 of the sleeve member 12 is bonded or otherwise secured within the bore 26 at the end 14 of the body portion 20 to form a leak-tight fit.

It should be noted that the body portion 20 primarily facilitates handling of the sheath 10 and, if desired, can be omitted to save material. Thus the sleeve member 12 can be joined directly to the collar portion 18, resulting in an abbreviated bore 26.

Figure 3:
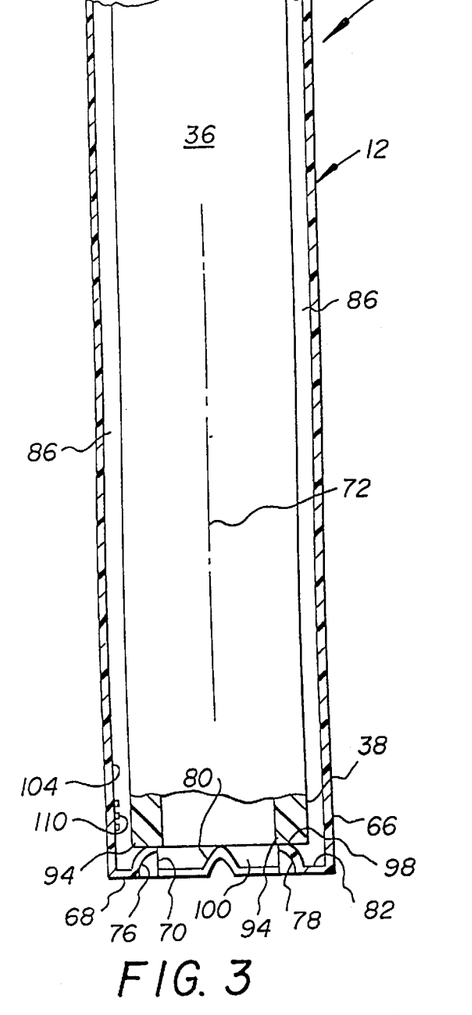
FIG. 3 is a sectional view of a sleeve member that forms a part of the disposable endoscope sheath.
Figure 4:
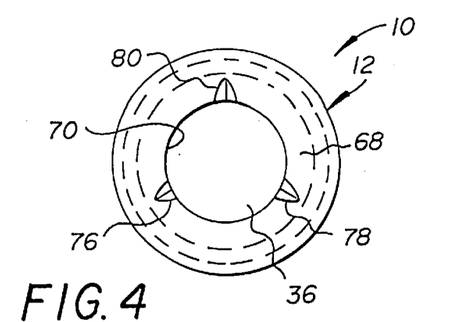
FIG. 4 is an end view of the sleeve member of FIG. 3.

Referring to FIGS. 3 and 4, a distal portion 66 of the sleeve member 12 includes a terminal annular flange 68 that defines a circular end opening 70. The opening 70 is of smaller diameter than the outside diameter of the endoscope shaft 36 to prevent the shaft 36 from extending beyond the terminal flange 68. The flange 68 is also sized and shaped to avoid obstructing the field of view of the endoscope shaft 36.

The terminal flange 68 makes an angle of approximately 90° with an elongated axis 72 of the sleeve member 12 and is formed with three spacer dimples 76, 78 and 80, spaced approximately 120° apart. The dimples 76, 78 and 80, which can be formed by indentation, project approximately 0.005 to 0.020 inches from an inner surface 82 of the flange 68. This results in a distal gap or end space 100 in the size range of 0.005 to 0.020 inches.

Although the number of dimples provided on the flange 68 is preferably three, a greater or lesser number can be used, such as 1 to 10. The shape of the dimples 76, 78 and 80 can be round, triangular or any other configuration which projects the specified amount from the inner surface 82.

In using the disposable sheath 10, the distal end portion 38 of the endoscope shaft 36 is aligned with the recess 24 of the sleeve housing 16 and inserted through the bore 26 of the body portion 20 into the hollow interior 28 of the sleeve member 12.

The internal diameter of the bore 26 and the internal diameter of the sleeve 12 are of greater magnitude than the outside diameter of the endoscope shaft 36 by a predetermined amount of approximately 0.002 inches to 0.012 inches. The diametrical difference between the bore 26 and the shaft 36, and between the sleeve interior 28 and the shaft 36 establishes a substantially annular irrigation channel or space 86 which extends from the fluid passage 54 in the collar 18 to the distal end portion 66 of the sleeve member 12.

Referring to FIGS. 2 and 3, the length of the endoscope shaft 36 is measured from a terminal end 92 at the housing 32 to an opposite terminal end 94 at the distal end portion 38.

The terminal end 94 is also referred to as the viewing end or the tip of the endoscope.

The disposable sheath 10 has a receiving length for the endoscope shaft 36 within the bore 26 and within the sleeve member 12. The receiving length for the endoscope shaft 36 is measured from a base 96 of the recess 24 to the crests 98 of the spacer dimples 76, 78 and 80 on the terminal flange 68 of the sleeve member 12.

The sheath 10 operates compatibly with the endoscope 32 when the endoscope shaft 36 is longer than the receiving length of the sheath 10. Thus, full insertion of the shaft 36 in the sheath 10 will cause the terminal end 94 of the endoscope shaft 36 to bottom against or engage the dimples 76, 78 and 80 without causing the endoscope housing 32 to bottom against the base surface 96 of the recess 24, as shown in FIG. 2.

Engagement between the terminal end 94 of the endoscope shaft 36 and the dimples 76, 78 and 80 is thus assured for a multiplicity of different endoscope shafts that are longer than the shaft receiving length of the sheath 10. Thus there is no need to precisely match a sheath 10 with an endoscope 34 based on shaft length, since the sheath 10 does not require the endoscope shaft 36 to have a specific matched length. Under this arrangement a predetermined distal gap or end space 100 (FIG. 3) is established between the terminal end 94 of the endoscope shaft 36 and the annular flange 82 of the sleeve member 12, for any number of different endoscope shaft lengths that bottom against the dimples 76, 78 and 80.

Irrigation fluid such as saline is pumped or pulsed in any suitable known manner through the irrigation tube 52 to the fluid passage 54 and into the annular irrigation channel 86. The channel 86 extends through the bore 26 of the body portion 20 and through the interior 28 of the sleeve member 12 for communication with the end opening 70 of the sleeve member 12.

Before irrigation fluid in the irrigation channel 86 is expelled through the end opening 70, it is diverted through the distal gap 100 across the terminal end 94 of the endoscope shaft 36 by the flange 68. The diverted irrigation fluid flushes surgical debris from the terminal end 94 of the endoscope shaft 36.

Since the dimples 76, 78 and 80 have a predetermined height or projection, they hold the terminal end 94 of the endoscope shaft 36 in a corresponding predetermined step-back position from the inner surface 82 of the flange 68 to provide the desired magnitude of the distal gap 100. Thus the distal gap 100 has a magnitude of approximately 0.005 to 0.020 inches and, in cooperation with the flange 68 at the distal end portion 66 of the sleeve member 12, enable the flow of irrigation fluid from the annular irrigation channel 86 to be redirected across the terminal end 94 of the endoscope shaft 36. The redirected flow of irrigation fluid provides an optimum flushing action to remove any surgical debris that accumulates at the endoscope viewing tip during a surgical procedure.

The predetermined step-back of the endoscope tip 94 also facilitates suction removal of a fluid droplet from the endoscope viewing end 94. For example, in some instances a drop of irrigation fluid may be left at the viewing end 94 of the endoscope shaft 36 when a flush cycle is completed. Since a field of view is taken through the viewing end 94, the residual drop of irrigation fluid can impede vision through the endoscope. Thus a slight suction pulse at the irrigation tube 52 will draw the obscuring droplet of irrigation fluid back into the irrigation channel 86. The flange 68 facilitates suction of the droplet from the viewing end 94 of the endoscope shaft 36.

If desired, an anti-fogging coating can be provided at the viewing end of the endoscope to help assure complete retraction of irrigation fluid from the viewing end 94 of the endoscope shaft 36 during a suction pulse.

The size of the irrigation channel 86 and the wall thickness of the sleeve member 12 are selected to provide a minimally intrusive low profile endoscope sheath for the endoscope shaft. Furthermore, by limiting the size of the irrigation channel 86 to the specified size range, irrigation solution passing into the annular channel 86 tends to remain stationary when the pumping or pulsing of irrigation fluid at the irrigation tube 52 ceases. Thus irrigation fluid does not drip uncontrollably out of the end opening 70 when irrigation activity ceases.

The preferred size of the irrigation channel 86 is not intended to accommodate suction removal of surgical debris from the surgical site or from the viewing end 94 of the endoscope. Removal of surgical debris by suction generally requires a channel having a size that might permit irrigation fluid to drip from the sheath when pumping ceases. Thus a combination irrigation and suction channel for removing surgical debris would normally be of a size that significantly increases the profile of the sheath.

Optionally, some or all of the inner surface of the bore 26 and/or the sleeve member 12 can be treated with a hydrophilic or other suitable coating to enhance retention of irrigation fluid when irrigation pump activity ceases. Alternatively, a fluid retention surface texture can be provided at the inner surface of the sheath 10 for fluid retention purposes.

For example, a selected portion of the inner surface 104 (FIG. 3) at the distal end 66 of the sleeve member 12 can include score marks, pits, protrusions, or an etched or rough surface, all of which are schematically shown at reference number 110, to help capture residual solution in the irrigation channel 86 when irrigation pump activity ceases.

When an endoscopically assisted surgical procedure is completed, the entire sheath 10 can be discarded along with the endoscope shaft 36. Thus there is no need to engage in time consuming, inconvenient and expensive sterilization procedures.

Figure 5:
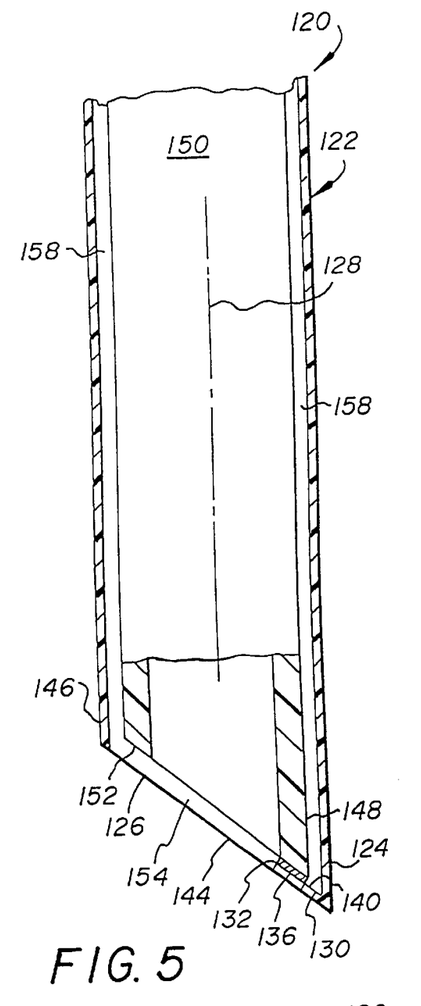
FIGS. 5–25 show sleeve members in sectional view and end view employed in further embodiments of the disposable sheath; the sleeve housing of FIGS. 1 and 2 being common to these embodiments is omitted for purposes of simplification.
Figure 6:
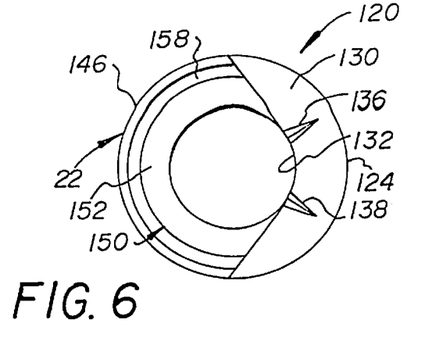

Another embodiment of the disposable sheath for an endoscope is generally indicated by the reference number 120 in FIGS. 5 and 6. The sheath 120 includes a sleeve member 122 joined to a sleeve housing (not shown) that is identical to the sleeve housing 16. The joining arrangement between the sleeve member and sleeve housing of this and other embodiments of the invention is identical to that of the sheath 10.

The sleeve member 122 has a distal portion 124 with a terminal end 126 that is inclined to the longitudinal axis 128 of the sleeve member 122, at an angle of approximately 5° to 70°. The terminal end 126 includes a similarly inclined flange 130. A terminal end 152 of an endoscope shaft 150 is inclined at an angle similar to that of the terminal end of the sleeve member 122.

As most clearly shown in FIG. 6, the flange 130 has a circumferential range of less than 360° with respect to the center of the sleeve member 122. Preferably the flange 130 has a circumferential range of approximately 90°–180° that encompasses the lowest portion of the inclined terminal end 126 as shown in FIG. 5.

The flange 130 includes a curved inner edge 132 and a pair of spacer dimples 136 and 138 that project a predetermined amount from an inner surface 140 of the flange 130. The dimples 136 and 138 project an amount that is equivalent to the projection specified for the dimples 76, 78 and 80 of the sleeve member 12.

An end opening 144 is defined between the curved inner edge 132 of the flange 130 and a wall 146 of the sleeve member 122. The flange 130 is sized to interfere with a distal portion 148 of the endoscope shaft 150 that is inserted in the sleeve member 122, to prevent the shaft 150 from extending beyond the opening 144 of the sleeve member 122. The flange 130 is also sized and shaped to avoid obstructing the field of view of the endoscope shaft 150.

The spacer dimples 134 and 136 are located in a predetermined position on the flange 130 to engage the terminal end 152 of the endoscope shaft 150. Such engagement results in a step-back of the terminal end 152 from the inner surface 140 by the amount previously specified for the sheath 10. The step-back of the terminal end 152 of the endoscope shaft 150 from the inner surface 140 of the flange 130 establishes a distal gap or space 154 of corresponding magnitude between the terminal end 152 and the inner surface 140.

In using the sheath 120, the endoscope shaft 150 is inserted into the sleeve housing (not shown) and into the sleeve member 122 in a manner similar to that described for the sheath 10. A substantially annular irrigation channel or space 158 dimensionally similar to the irrigation channel 86 is established between the endoscope shaft 150 and the sleeve member 122. The terminal end 152 of the endoscope shaft engages the spacer dimples 136 and 138, to establish the distal gap 154.

Irrigating fluid that is pulsed or pumped into the irrigation channel 158 from the sleeve housing (not shown), exits from the sleeve member 122 through the end opening 144. Some portions of the irrigation fluid that exit from the end opening 144 are diverted across the terminal end 152 of the endoscope shaft 150 by the flange 130. Other portions of irrigation fluid that do not impinge on the flange 130 can flow onto the terminal end 152 because of the optimum size of the distal gap 154.

The movement of fluid across the terminal end 152 of the endoscope shaft 150 provides a flushing action at the terminal end that cleans away any surgical debris. Similarly, the flange 130 facilitates suction of irrigation fluid droplets from the terminal end 152 of the endoscope shaft 150 to prevent obscurance of the field of view by any irrigation fluid that accumulates thereon.

The sheath 120 otherwise operates in a manner similar to that previously described for the sheath 10.

It should be noted that the step back of the endoscope shaft 150 from the terminal end 126 provided by the dimples 136 and 138 is not a necessity on flange 130 with distal portions inclined in the range of approximately 25°–70° because the flange 130 holds the endoscope shaft 150 back from the terminal end 126. Irrigation fluid can thus exit from the sleeve member 122 at the end opening 144. If desired, the flange 130 can have a 360° range and in this case, spacer dimples such as 136 and 138 would be desirable.

Figure 7:
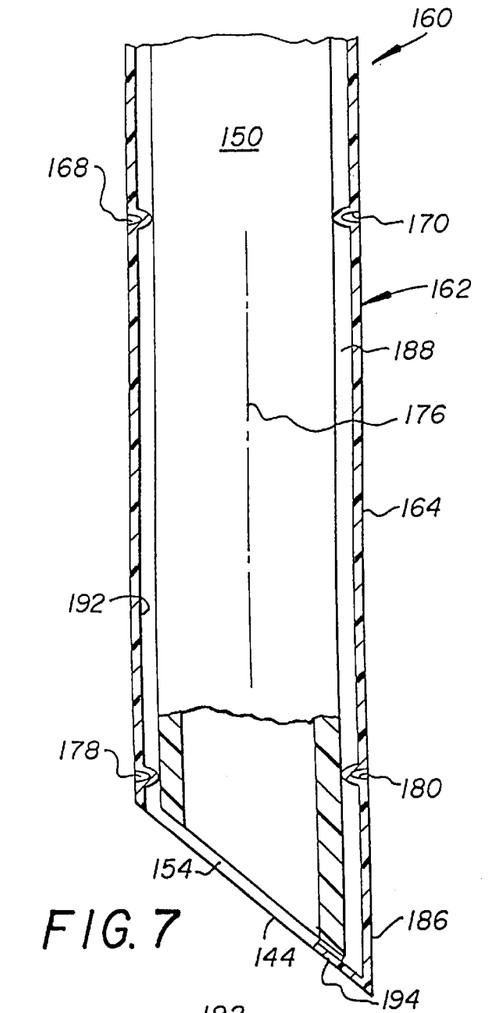
Figures 8, 10:
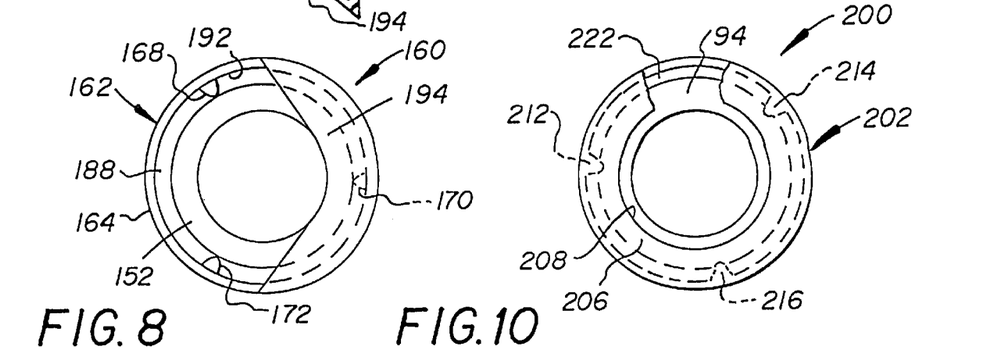

A further embodiment of the disposable sheath for an endoscope is generally indicated by the reference number 160 in FIGS. 7 and 8. The sheath 160 includes a sleeve member 162 joined to a sleeve housing (not shown) that is identical to the sleeve housing 16.

The sleeve member 162 includes a tubular wall 164 having a set of centering dimples such as 168, 170 and 172 spaced approximately 120° apart and provided at a first axial location with respect to a longitudinal axis 176 of the sleeve member 162. A second set of similarly spaced centering dimples, such as the dimples 178 and 180, are provided at a second axial location proximate a distal portion 186 of the sleeve member 162. The axial spacing between the first and second set of centering dimples is approximately 1 to 5 inches.

If desired, the centering dimples can be provided in a non-opposed longitudinally staggered arrangement. It should also be noted that centering dimples can be provided on any of the sleeve members disclosed herein.

When the endoscope shaft 150 is disposed in the sleeve member 162, an annular irrigation channel 188 is established that is dimensionally similar to the irrigation channel 86.

The centering dimples 168, 170, 172 and 178, 180 project from an inner surface 192 by a predetermined amount that is less than the size of the irrigation channel and help center the endoscope shaft 150 that is positioned in the sleeve member 162.

The sleeve member 162 also includes an end flange 194 similar to the end flange 130 of the sleeve member 122 with spacer dimples (not shown) similar to the spacer dimples 136 and 138.

As an alternative to the centering dimples 168, 170, 172, 178 and 180, the sleeve member 162 can include axially elongated centering projections (not shown) that extend the entire axial distance of the sleeve member wall 164 or a portion of the axial distance to provide a centering function similar to that provided by the centering dimples.

In all other respects the structure and operation of the sheath 160 including the sleeve member 162 are similar to those of the sheaths 10 and 120.

Figure 9:
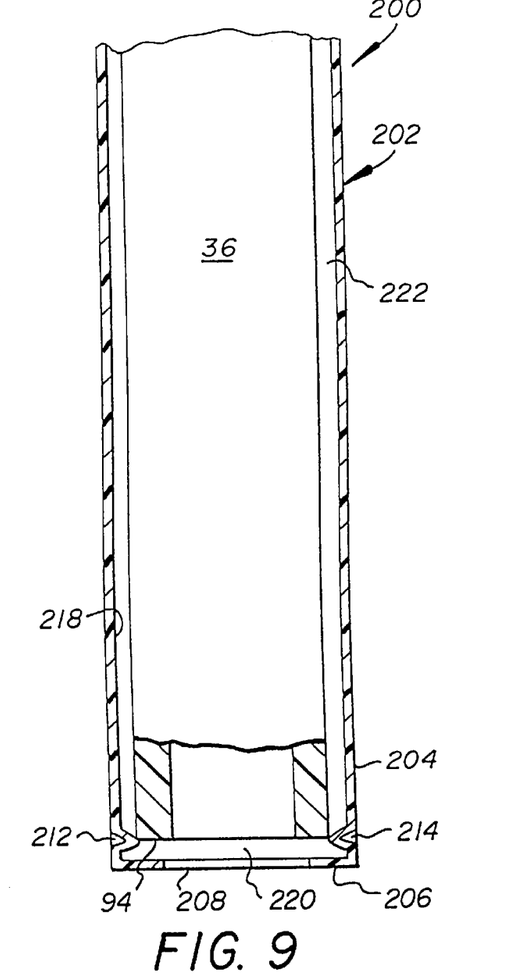

Still another embodiment of the disposable sheath for an endoscope is generally indicated by the reference number 200 in FIGS. 9 and 10. The sheath 200 includes a sleeve member 202 joined to a sleeve housing (not shown) that is identical to the sleeve housing 16.

The sleeve member 202 includes a distal portion 204 having an annular terminal end flange 206 that defines an end opening 208. A set of spacer dimples 212, 214 and 216 spaced approximately 120° apart are provided proximate the end flange 206. The projection of the spacer dimples 212, 214 and 216 from an inside surface 218 of the sleeve member 202 interferes with the endoscope shaft 36 to prevent passage of the terminal end portion 94 of the endoscope shaft 36 beyond the spacer dimples 212, 214 and 216.

The spacer dimples 212, 214 and 216 are at a predetermined location that establishes a gap 220 of similar magnitude to the gap 100 between the endoscope terminal end 94 and the sleeve member end flange 206. The spacer dimples 212, 214 and 216 and the end flange 206 are also of a size that avoids obscuring the field of view through the endoscope end 94.

A substantially annular irrigation channel 222, dimensionally similar to the irrigation channel 86 of the sheath 10, is established between the endoscope shaft 36 and the inner surface 218 of the sleeve member 202. Except for the distal portion 204, the sleeve member 202 is structurally similar to the sleeve member 12.

In using the sheath 200, irrigation fluid (not shown) is directed into the irrigation channel 222 for exit at the end opening 208. Before the irrigation fluid exits from the opening 208, it enters the distal gap 220 and is diverted across the endoscope end 94 by the flange 206. The diverted fluid flushes debris from the endoscope end 94 to provide an effective cleaning action. Other aspects of the structure and operation of the sheath 200 are similar to those previously described for the sheath 10.

Figure 11:
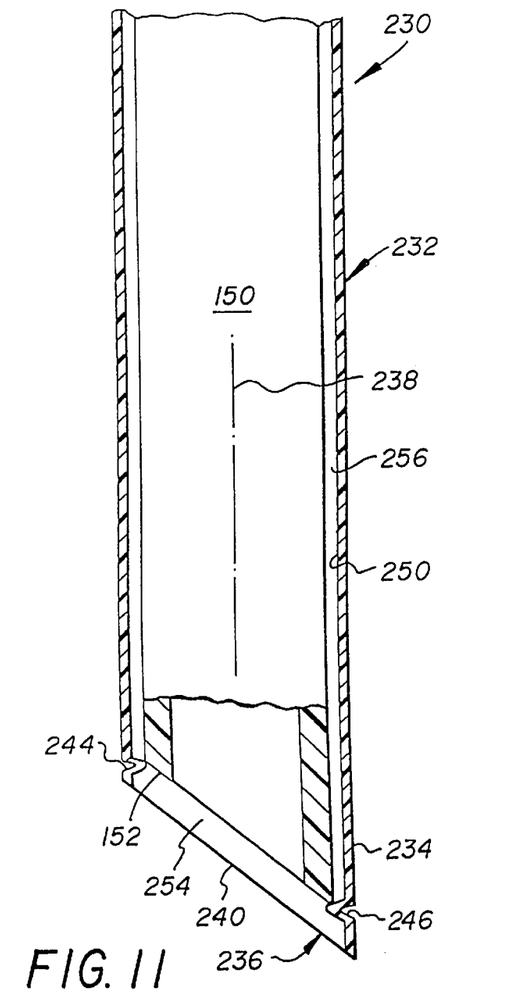
Figure 12:
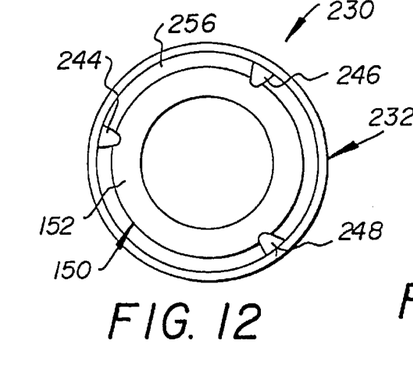

A still further embodiment of a disposable endoscope sheath is generally indicated by the reference number 230 in FIGS. 11 and 12. The sheath 230 includes a sleeve member 232 joined to a sleeve housing (not shown) that is identical to the sleeve housing 16.

The sleeve member 232 includes a distal portion 234 having a terminal end 236 inclined to a longitudinal axis 238 of the sleeve member 232. The inclination of the terminal end 236 to the longitudinal axis 238 is in the same angular range as that of the flange 130 in the sleeve member 122. An end opening 240 is defined at the terminal end 236.

A set of spacer dimples 244, 246 and 248 spaced approximately 120° apart as shown in FIG. 12, project from an inside surface 250 of the sleeve member 232 to prevent passage of the terminal end portion 152 of the endoscope shaft 150 beyond the spacer dimples.

A distal gap 254, similar in magnitude to the distal gap 100 of the sheath 10, is thus established between the endoscope terminal end 152 and the sleeve member terminal end 236. The spacer dimples 244, 246 and 248 are of a size that avoids obscuring the field of view through the endoscope end 152.

Although the distal portion 234 has an inclined end 236, the general arrangement of the spacer dimples 244, 246 and 248 is similarly adaptable to a non-inclined terminal end arrangement.

An irrigation channel 256, dimensionally similar to the irrigation channel 86 of the sheath 10, is established between the endoscope shaft 150 and the inner surface 250 of the sleeve member 232. Except for the distal portion 234, the sleeve member 232 is structurally similar to the sleeve member 122 of the sheath 120.

In using the sheath 230, irrigation fluid directed into the irrigation channel 256 exits at the end opening 240. The exiting fluid tends to flow onto the endoscope end 152 due to optimal retraction of the endoscope end 152 within the sleeve member 232. Fluid can thus flow into the gap 254 and onto the endoscope end 152 thereby flushing debris from the endoscope end to provide an effective cleaning action. The sheath 230 is otherwise operationally similar to the sheath 120.

Figure 13:
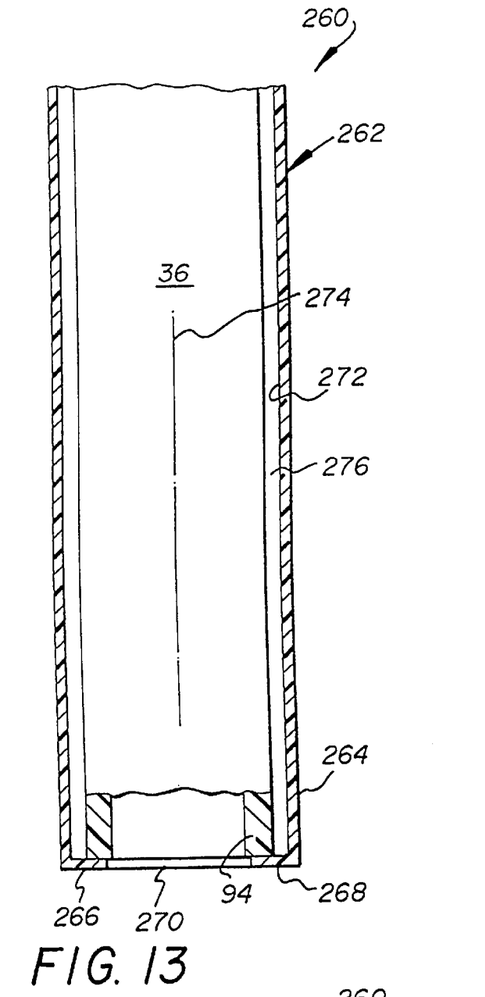
Figure 14:
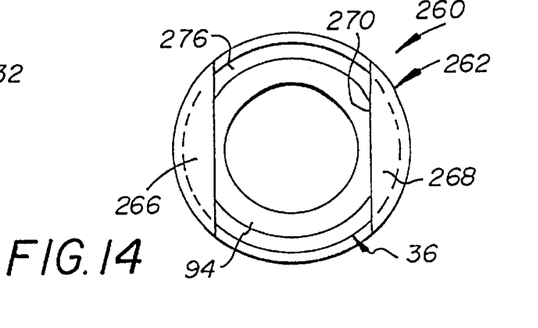

Another embodiment of the disposable endoscope sheath is generally indicated by the reference number 260 in FIGS. 13 and 14. The sheath 260 includes a sleeve member 262 joined to a sleeve housing (not shown) that is identical to the sleeve housing 16.

The sleeve member 262 includes a distal portion 264 having diametrically opposite flange portions 266 and 268 that define an end opening 270. The end flanges 266 and 268 are sized to prevent passage of the terminal end portion 94 of the endoscope shaft 36 beyond the end opening 270 without obscuring the field of view through the endoscope end 94.

A substantially annular irrigation channel 276 dimensionally similar to the irrigation channel 86 of the sheath 10 is defined between the endoscope shaft 36 and the inner surface 272 of the sleeve member 262.

Except for the distal portion 264, the sleeve member 262 is structurally similar to the sleeve member 12.

In using the sheath 260, irrigation fluid directed into the irrigation channel 276 exits at the end opening 270. As irrigation fluid exits from the end opening 270, it can flow onto the endoscope end 94 due to the predetermined recession of the shaft 36 in the sleeve member 262 and flush surgical debris from the endoscope end 94, thereby providing an effective cleaning action.

If desired, dimples (not shown) similar to the dimples of the sleeve members 12 and 122, can be provided at the end flanges 266 and 268 to establish a specified predetermined gap between the endoscope end 94 and the end flanges 266 and 268. In this manner, irrigation fluid can be diverted across the endoscope end 94 by the flanges 266 and 268 to flush away surgical debris from the endoscope end 94.

Figure 15:
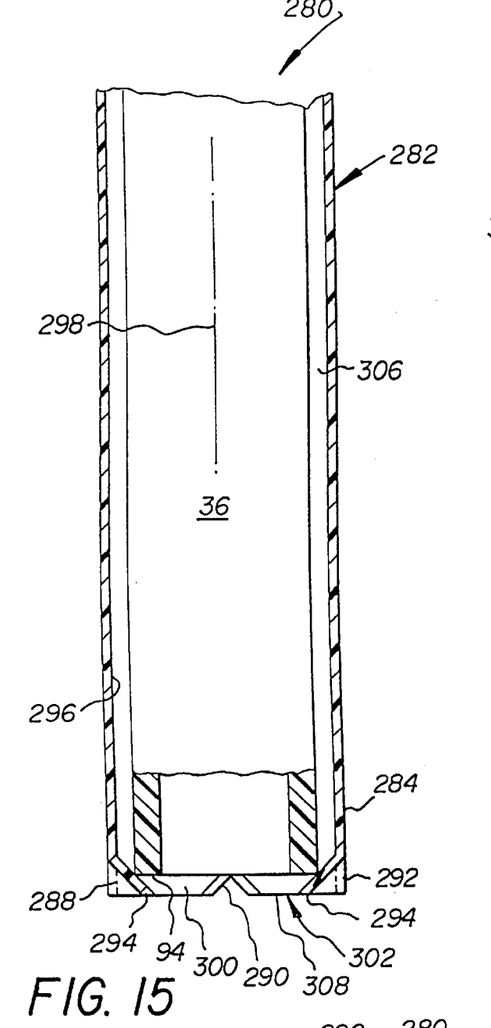
Figure 16:
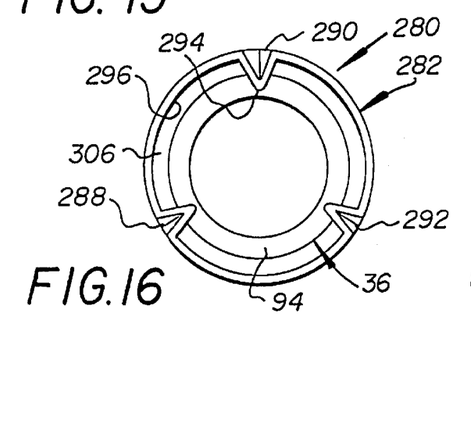

Another embodiment of a disposable endoscope sheath is generally indicated by the reference number 280 in FIGS. 15 and 16. The sheath 280 includes a sleeve member 282 joined to a sleeve housing (not shown) that is identical to the sleeve housing 16.

The sleeve member 282 includes a distal portion 284 with terminal deformations 288, 290 and 292 spaced approximately 120° apart. The deformations 288, 290 and 292 are V-shaped in end view as shown in FIG. 16 and can be inclined approximately 20° to 90° as shown in FIG. 15. It should be noted that the number of deformations used can be as few as one or as many as 30.

A tip portion 294 of the deformations 288, 290 and 292 extends from an inner wall surface 296 of the sleeve member 282 toward an axis 298 an amount that prevents passage of the terminal end portion 94 of the endoscope shaft 36 beyond the deformations 288, 290 and 292 without obscuring the field of view through the endoscope end 94.

The angle of the deformations 288, 290 and 292 and the extent of the tip portions 294 are also selected to provide a distal gap 300 that is dimensionally similar to the gap 100 between the endoscope terminal end 94 and a terminal end 302 of the sleeve member 282.

A substantially annular irrigation channel 306, dimensionally similar to the irrigation channel 86 of the sheath 10, is established between the endoscope shaft 36 and the inner surface 296 of the sleeve member 282. Except for the distal portion 284, the sleeve member 282 is structurally similar to the sleeve member 12.

In using the sheath 280, irrigation fluid directed into the irrigation channel 306 exits at an end opening 308 of the sleeve member 282. The exiting fluid flows onto the endoscope end 94 to provide an effective cleaning action. The distal gap 300, being within the predetermined size range, helps assure the effectiveness of the flushing action.

Figure 17:
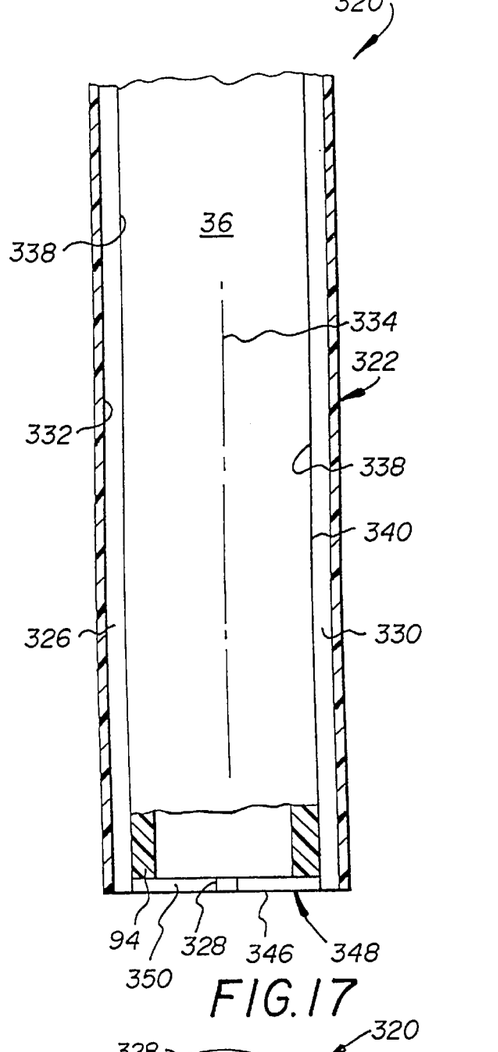
Figure 18:
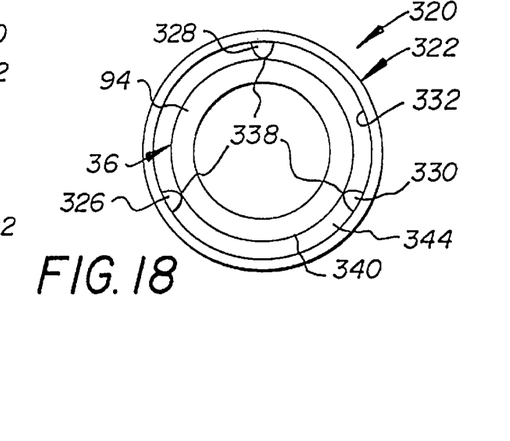

A still further embodiment of the disposable sheath for an endoscope is generally indicated by the reference number 320 in FIGS. 17 and 18. The sheath 320 includes a sleeve member 322 joined to a sleeve housing (not shown) that is identical to the sleeve housing 16.

The sleeve member 322 includes a series of spines, splines or ridges 326, 328 and 330 that extend from one end of the sleeve member 322 to the other end. The spines 326, 328 and 330, which can be formed by extruding or injection molding the sleeve member 322, project radially inwardly such that the inner diameter of the spines is approximately 0.001 to 0.020 inches larger than the outer diameter of the endoscope shaft 36. The number of spines used can be as few as one or as many as 100.

If the sleeve member is made of elastomeric material, the inner diameter of the spines can be 0.001 to 0.010 inches smaller than the diameter of the endoscope shaft 36 to provide a detent grip that secures the endoscope shaft 36 in position during use.

A longitudinal engaging surface 338 of the spines 326, 328 and 330 engages an outer surface 340 of the endoscope shaft 36 to detent the shaft in a selected slidable position within the sleeve member 322. The endoscope shaft 36 can thus be positionally located and held in a selected axial position within the sleeve member 322 by the spines 326, 328 and 330.

An irrigation channel 344 (FIG. 18) dimensionally similar to the irrigation channel 86 is established between the outer surface 340 of the endoscope shaft 36 and the inner surface 336 of the sleeve member 322.

In using the sheath 320, irrigation fluid directed into the irrigation channel 344 exits at an end opening 346 of the sleeve member 322. The endoscope shaft 36 is placed in a predetermined position in the sleeve member 322 by aligning the terminal end 94 of the endoscope shaft 36 with a terminal end 348 of the sleeve member 322 and slightly retracting the endoscope shaft 36 to establish a gap 350 in the preferred size range between the endoscope end 94 and the sleeve member end 348. Any suitable mark (not shown) can be provided on the sleeve member 322 to indicate the desired retraction position of the endoscope end 94.

The irrigation fluid, as it exits through the end opening 346, flows onto the endoscope end 94 to provide a flushing action that cleans surgical debris from the endoscope end 94.

It has also been found that a cleaning action is obtainable with the endoscope end 94 located flush with the sleeve member end 348 or with the endoscope end 94 projecting approximately 0.001 to 0.010 inches beyond the sleeve member end 348.

Figures 19, 20, 21, 22:
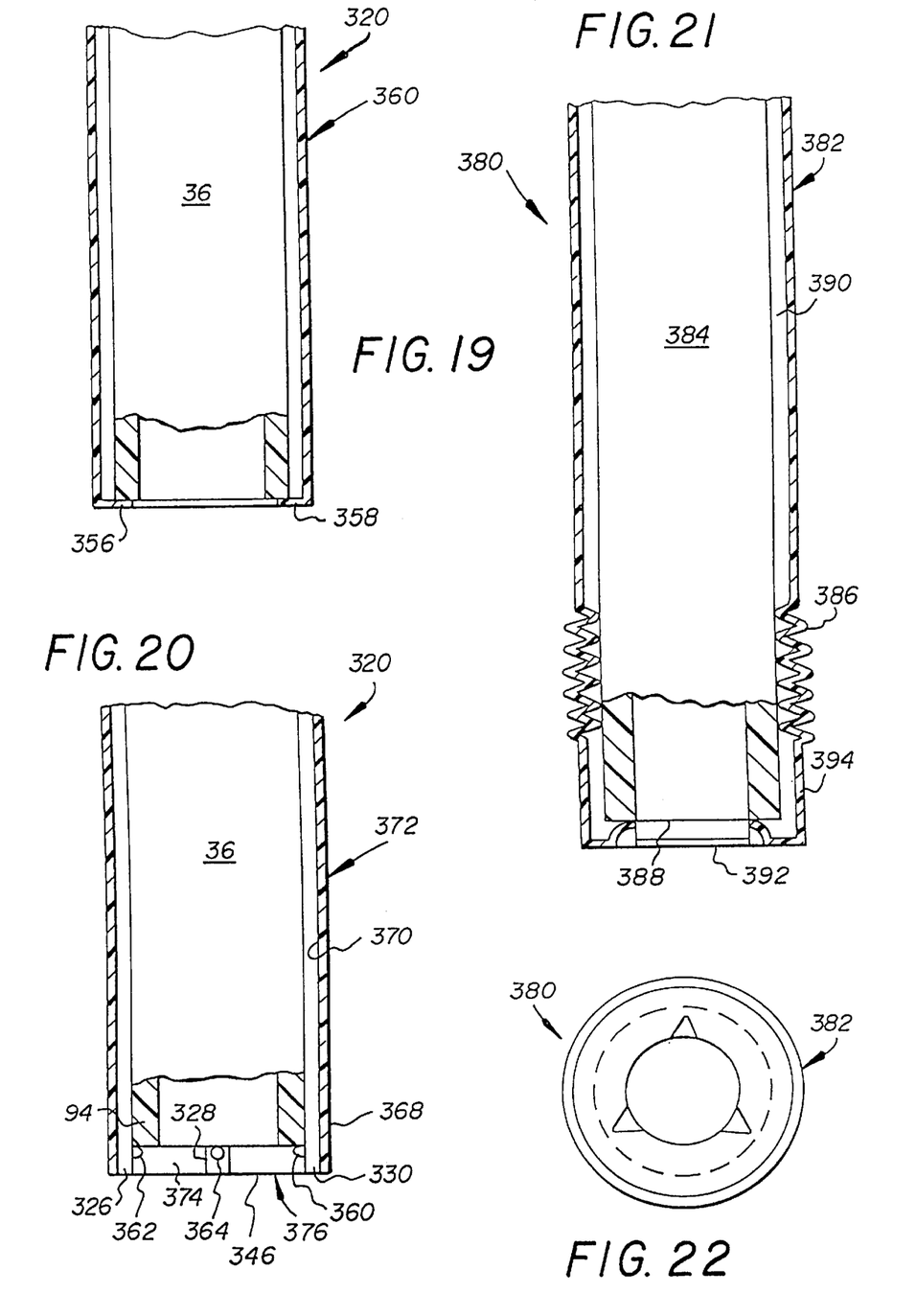

A modification of the sleeve member 322, indicated by the reference number 360 in FIG. 19, includes end flanges 356 and 358 similar to the end flanges 266 and 268 of the sleeve member 262. Except for the end flanges 356 and 358, the sleeve member 360 is structurally similar to the sleeve member 322 and operation of the sleeve member 360 is similar to that described for the sleeve member 262.

A further modification of the sleeve member 322, indicated by the reference number 372 in FIG. 20, includes dimples 362, 364 and 366 at a distal portion 368. The dimples 362, 364 and 366 are provided on the spines 326, 328 and 330 to prevent the end portion 94 of the endoscope shaft 36 from passing through the end opening 346. If desired, suitably sized shaft engaging dimples (not shown) can be formed on the inner surface 370 of the sleeve member 372. When the endoscope shaft 36 is positioned in the sleeve member 372 and engages the dimples 362, 364 and 366, a distal gap 374 dimensionally similar to the gap 100 is established between the endoscope end portion 94 and a terminal end 376 of the sleeve member 372.

In using the sheath 320 with the modified sleeve member 372, irrigation fluid that exits through the end opening 346 passes through the gap 374 and can flow upon the endoscope end 94 to flush debris therefrom in a manner similar to that previously described for the sheath 230.

Another embodiment of the disposable sheath for an endoscope is generally indicated by the reference number 380 in FIGS. 21 and 22. The sheath 380 includes a sleeve member 382 joined to a sleeve housing (not shown) that is identical to the sleeve housing 16.

The sleeve member 382 is formed of a flexible elastomeric material such as polyvinylchloride and is sized to accommodate a flexible endoscope shaft 384 to establish an irrigation channel 390 dimensionally similar to the channel 86. The sleeve member 382 has a wall thickness in the range of approximately 0.002 to 0.010 inches to assure flexibility and bendability and can include an optional accordion or bellows section 386 to accommodate relatively sharp bends in a flexible endoscope that are typically encountered approximately ½ inch from the endoscope end 388. The bellows section 386, although shown in exaggerated scale, has sufficient clearance from the endoscope shaft 384 to permit irrigation fluid in the irrigation channel 390 to flow to the terminal opening 392 of the sleeve 382.

Figures 23, 24:
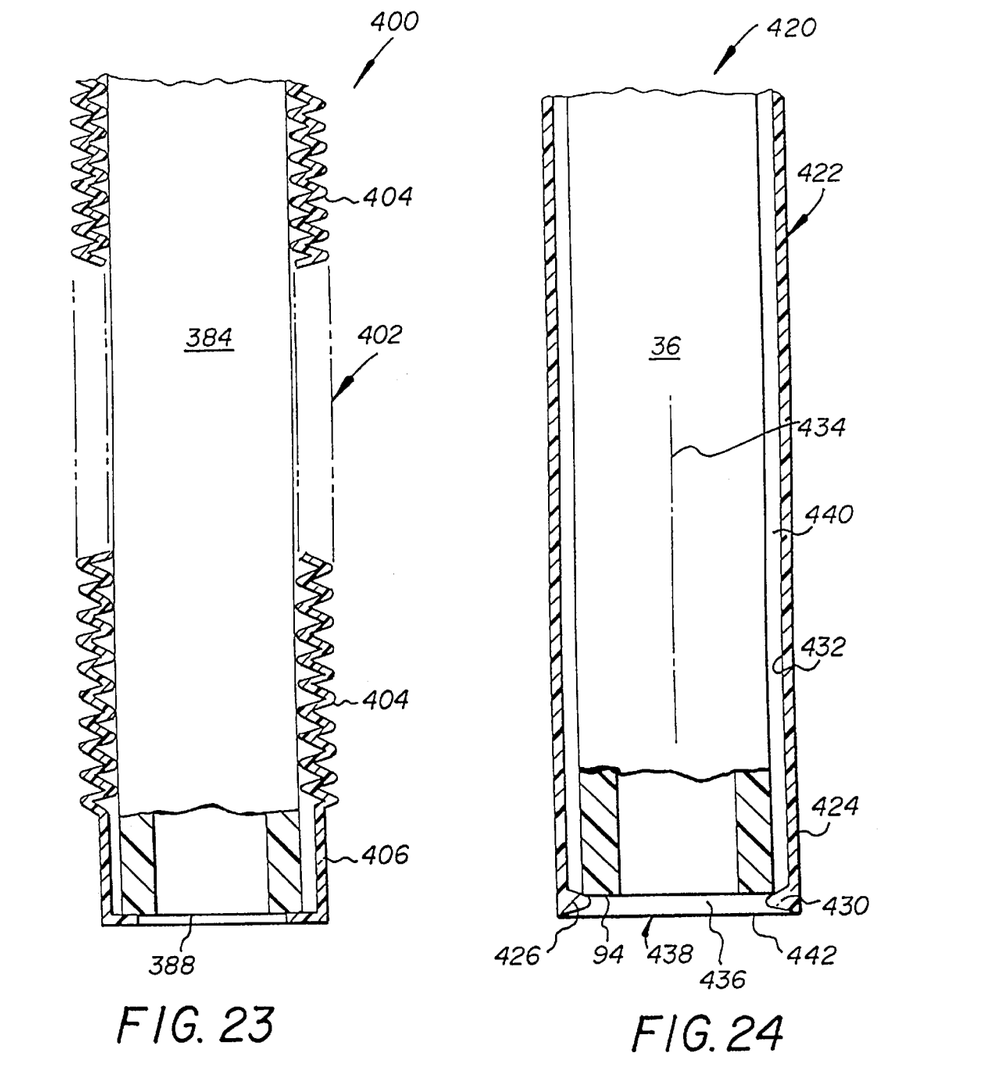

If desired, the accordion or bellows section 386 can extend the entire length of the sleeve member as shown in FIG. 23.

The sleeve member 382 further includes a distal portion 394 that is identical to the distal portion 66 of the sheath 10.

The distal end portions of any of the previously disclosed embodiments can be used with a flexible sleeve member of the type shown in FIGS. 21 and 23.

Thus, for example, FIG. 23 shows a sheath 400 with a sleeve member 402 having a substantially full length bellows or accordion section 404 and a distal end portion 406 similar to the distal end portion 264 of the sheath 260.

Operation of the sheaths 380 and 400 is similar to the operation of the sheaths 10 and 260.

Figure 25:
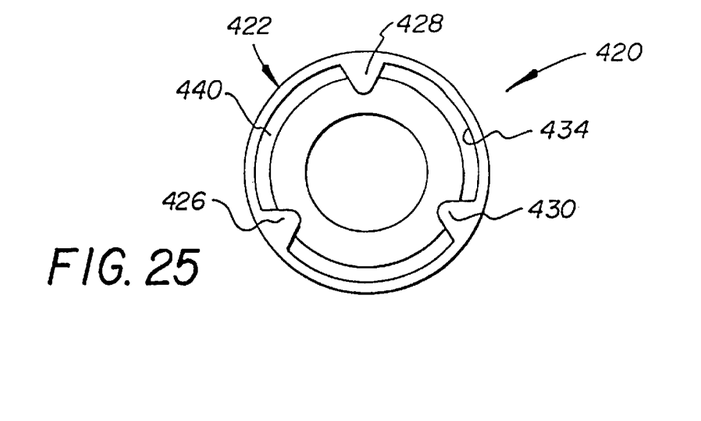

Another embodiment of a disposable endoscope sheath is generally indicated by the reference number 420 in FIGS. 24 and 25. The sheath 420 includes a sleeve member 422 joined to a sleeve housing (not shown) that is identical to the sleeve housing 16.

The sleeve member 422 includes a distal portion 424 with terminal dimples 426, 428 and 430 spaced approximately 120° apart. The dimples 426, 428 and 430 can be molded or formed by indentation.

The dimples 426, 428 and 430 extend from an inner wall surface 432 of the sleeve member 422 toward an axis 434 an amount that prevents passage of the terminal end portion 94 of the endoscope shaft 36 beyond the dimples 426, 428 and 430 without obscuring the field of view through the endoscope end 94.

The dimples 426, 428 and 430 are also formed to provide a distal gap 436 that is dimensionally similar to the gap 100 between the endoscope terminal end 94 and a terminal end 438 of the sleeve member 422.

A substantially annular irrigation channel 440, dimensionally similar to the irrigation channel 86 of the sheath 10, is established between the endoscope shaft 36 and the inner surface 432 of the sleeve member 422. Except for the distal portion 424, the sleeve member 422 is structurally similar to the sleeve member 12.

In using the sheath 420, irrigation fluid directed into the irrigation channel 440 exits at an end opening 442 of the sleeve member 422. The exiting fluid flows onto the endoscope end 94 to provide an effective cleaning action. The distal gap 436, being within the predetermined size range, assures effective flushing action.

Although this embodiment and other embodiments disclosed herein show the use of three dimples, it should be noted that as few as one or as many as 10 dimples can be used.

Some advantages of the invention evident from the foregoing description include a disposable sheath that enables the endoscope to be positioned at an optimum location with respect to a sleeve. The endoscope can be slightly recessed in some embodiments, or flush with the terminal end of the sleeve in other embodiments. In some instances the endoscope can project a predetermined amount from the sleeve. Thus irrigation fluid exiting along the perimeter is attracted to itself and can flow onto the viewing end of an endoscope to flush surgical debris from the viewing end. The sleeve member of the sheath is a low profile structure and thus does not require any significant enlargement of a surgical incision to accommodate the endoscope and sleeve. A further advantage is that the sleeve member need not be customized to different lengths of an endoscope and can accommodate a variety of different endoscope lengths that are longer than the sleeve member. The sleeve can also be adapted to accommodate endoscopes with barrels that differ in outside diameter by 0.001 to 0.005 inches. The disposable sheath is economical to manufacture and saves time and money by eliminating the need to use sterilizable components. The invention is also adaptable to endoscopes that have inclined or non-inclined terminal portions.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A sheath for an endoscope comprising
   a) a disposable elongated sleeve sized to accommodate an endoscope shaft having a light transmitting member and a viewing end, said sleeve having a predetermined length and a distal portion with a free terminal end and being of generally circular cross section with a predetermined inner diameter, such that an annular irrigation space of predetermined size ranging from about 0.002 inches to about 0.012 inches is defined between said sleeve and the endoscope shaft when said sleeve receives the endoscope shaft,
   b) the terminal end of the sleeve having at least one opening,
   c) the distal portion of said sleeve having flange means at the terminal end of said sleeve to maintain the endoscope shaft in a stopped predetermined position in the sleeve, said flange means comprising a flange and a plurality of spacer members of predetermined size provided on said flange and extending away from said flange to engage the viewing end of said endoscope shaft to step away the viewing end of the endoscope shaft a predetermined distance from the flange and establish a distal gap ranging from about 0.005 inches to about 0.020 inches between the stepped away viewing end of the endoscope shaft and the flange such that the flange directs irrigation fluid from the irrigation space directly into the distal gap and onto the viewing end of the endoscope to flush surgical debris from the viewing end of the endoscope, through the terminal end opening of the sleeve, said annular irrigation space being sized to retain the irrigation solution by means of surface tension when it is no longer being directed into said irrigation space.

2. The sheath as claimed in claim 1 including detent means to hold the endoscope shaft in a axially aligned position within said sleeve said detent means comprising projecting means formed on an inner surface of said sleeve to grip and hold the endoscope shaft in said axially aligned position.

3. The sheath as claimed in claim 1 wherein said flange has a configuration which is substantially semi annular.

4. The sheath as claimed in claim 1 wherein said flange is of annular shape.

5. The sheath as claimed in claim 1 wherein said sleeve is formed of a rigid material.

6. The sheath as claimed in claim 1 wherein said sleeve has an inner surface and the inner surface has formations selected from the group consisting of coatings, score marks, pits, etching and roughness to provide said inner surface with hydrophilic or solution retention characteristics.

7. A sheath for an endoscope comprising
   a) a disposable elongate sleeve sized to accommodate an endoscope shaft having a light transmitting member and a viewing end, said sleeve having a predetermined length and a distal portion being of generally circular cross section with a longitudinal axis and a predetermined inner diameter, said distal portion of said sleeve being formed with a terminal end inclined at an angle ranging from 5° to 70° to the longitudinal axis of said sleeve and formed with an inwardly projecting flange portion such that a predetermined irrigation space is defined between said sleeve and the endoscope shaft when said sleeve receives the endoscope shaft,
   b) the terminal inclined end flange portion having a circumferential range of less than 360° with respect to said longitudinal axis,
   c) said flange portion being provided with means for stepping the viewing end of the endoscope shaft away from the flange in a predetermined retracted position in the sleeve to establish a distal gap of predetermined magnitude between the flange portion and the viewing end of the endoscope such that irrigating solution directed into the irrigation space can be redirected by said flange to flow onto the viewing end of the endoscope to flush surgical debris from the viewing end of the endoscope through the terminal end opening of the sleeve.

8. The sheath as claimed in claim 7 wherein said stepping means include a predetermined number of dimples projecting from said flange within said sleeve.

9. A method of cleaning surgical debris from the viewing end of an endoscope comprising the steps of
   a) inserting the endoscope shaft in a disposable endoscope sheath having a sleeve for receiving the endoscope shaft to establish an irrigation space between the sleeve and shaft, with the viewing end of the endoscope shaft stepped from a terminal end of the sleeve to establish a predetermined distal gap between the viewing end of the endoscope shaft and the terminal end of the sleeve,
   b) directing irrigation fluid into the irrigation space for movement toward the viewing end of the endoscope shaft,
   c) locating the viewing end of the endoscope shaft at a predetermined position with respect to the sleeve member where the irrigation fluid can flow onto the viewing end to flush away surgical debris from the endoscope shaft,
   d) providing the sleeve member with an inside diameter that together with the outside of the endoscope shaft enables the irrigation space to retain irrigation fluid by capillary action when the irrigation fluid is no longer being directed into the irrigation space; and
   e) initiating a suction pulse at the end of an irrigation fluid flush cycle to draw droplets of irrigation fluid back into the irrigation space.

10. The method of claim 9 wherein irrigation fluid is directed away from the viewing end of the endoscope shaft for a predetermined time interval to extract any fluid from the viewing end of the endoscope shaft.

11. A sheath for an endoscope comprising
a) an elongated sleeve formed of a flexible material with a flexible bellows positioned in at least one distinct area along said elongated sleeve, said elongated sleeve being sized to accommodate an endoscope shaft having a light transmitting member and a viewing end, said sleeve having a predetermined length and a distal portion with a free terminal end and being of generally circular cross section with a predetermined inner diameter, such that an irrigation space of predetermined size is defined between said sleeve and the endoscope shaft when said sleeve receives the endoscope shaft,
b) the terminal end of the sleeve having at least one opening,
c) the distal portion of said sleeve having means to maintain the endoscope shaft in a predetermined position in the sleeve such that irrigating solution directed into the irrigation space can flow onto the viewing end of the endoscope to flush surgical debris from the viewing end of the endoscope through the terminal end opening of the sleeve, said irrigation space being sized to retain the irrigation solution when it is no longer being directed into said irrigation space.

12. A sheath for an endoscope comprising
a) an elongated sleeve sized to accommodate an endoscope shaft having a light transmitting member and a viewing end, said sleeve having a predetermined length and a distal portion with a free terminal end and being of generally circular cross section with a predetermined inner diameter, such that an irrigation space of predetermined size is defined between said sleeve and the endoscope shaft when said sleeve receives the endoscope shaft,
b) the terminal end of the sleeve having at least one opening,
c) the distal portion of said sleeve having means to maintain the endoscope shaft in a predetermined position in the sleeve such that irrigating solution directed into the irrigation space can flow onto the viewing end of the endoscope to flush surgical debris from the viewing end of the endoscope through the terminal end opening of the sleeve, said maintaining mans including means for engaging and stopping the viewing end of the endoscope in a selected predetermined position, said sleeve has a longitudinal axis and an inner surface, and said engaging and stopping means comprising a substantially semi-annular shaped flange projecting toward said longitudinal axis to engage the viewing end of an endoscope in the form of a flange, said flange being provided at the terminal end of said sleeve and is longitudinally spaced a predetermined amount from said projecting means to establish said distal gap between the terminal end of said sleeve member and the viewing end of said endoscope shaft when said sleeve receives said endoscope shaft, said irrigation space being sized to retain the irrigation solution when it is no longer being directed into said irrigation space.

13. A sheath for an endoscope comprising
a) an elongated sleeve sized to accommodate an endoscope shaft having a light transmitting member and a viewing end, said sleeve having a predetermined length and a distal portion with a free terminal end and being of generally circular cross section with a predetermined inner diameter, such that an irrigation space of predetermined size is defined between said sleeve and the endoscope shaft when said sleeve receives the endoscope shaft,
b) the terminal end of the sleeve having at least one opening,
c) the distal portion of said sleeve having means to maintain the endoscope shaft in a predetermined position in the sleeve such that irrigating solution directed into the irrigation space can flow onto the viewing end of the endoscope to flush surgical debris from the viewing end of the endoscope through the terminal end opening of the sleeve, said maintaining means include means for engaging and stopping the viewing end of the endoscope in a selected predetermined position, said sleeve has a longitudinal axis and an inner surface, and said engaging and stopping means including means projecting from said inner surface toward said longitudinal axis to engage the viewing end of an endoscope in the form of a flange being formed as diametrically opposed flange portions, said flange being provided at the terminal end of said sleeve and is longitudinally spaced a predetermined amount from said projecting means to establish said distal gap between the terminal end of said sleeve member and the viewing end of said endoscope shaft when said sleeve receives said endoscope shaft, said irrigation space being sized to retain the irrigation solution when it is no longer being directed into said irrigation space.

14. A sheath for an endoscope comprising
a) a reusable elongated sleeve sized to accommodate an endoscope shaft having a light transmitting member and a viewing end, said sleeve having a predetermined length and a distal portion with a free terminal end and being of generally circular cross section with a predetermined inner diameter, so that a cross section taken perpendicular to the axis of the sleeve yields an annular irrigation space between said sleeve and said endoscope shaft ranging from about 0.002 inches to about 0.012 inches is defined between said sleeve and the endoscope shaft when said sleeve receives the endoscope shaft,
b) the terminal end of the sleeve having at least one opening,
c) the distal portion of said sleeve having flange means at the terminal end of said sleeve to maintain the endoscope shaft in a stopped predetermined position in the sleeve, said flange means comprising a flange and a plurality of spacer members of predetermined size provided on said flange and extending away from said flange to engage the viewing end of said endoscope shaft to step away the viewing end of the endoscope shaft a predetermined distance from the flange and establish a distal gap ranging from about 0.005 inches to about 0.020 inches between the stepped away viewing end of the endoscope shaft and the flange such that the flange directs irrigation fluid from the irrigation space directly into the distal gap and onto the viewing end of the endoscope to flush surgical debris from the viewing end of the endoscope, through the terminal end opening of the sleeve, said annular irrigation space being sized to retain the irrigation solution by means of surface tension when it is no longer being directed into said irrigation space.

15. A sheath for an endoscope as claimed in claim 14 wherein said sleeve has a terminal end which is inclined at an angle of 5° to 70° with respect to the longitudinal axis of the sleeve, said flange being crescent shaped in configuration and secured to the distal area of the inclined terminal end of said sleeve acting as a stop for said viewing end of said endoscope.

* * * * *